(12) United States Patent
Kim et al.

(10) Patent No.: US 10,912,848 B2
(45) Date of Patent: *Feb. 9, 2021

(54) DUAL-PURPOSE PAT/ULTRASOUND CONTRAST AGENT BOUND WITH NANOPARTICLES CONTAINING DRUG AND METHOD FOR PREPARING SAME

(71) Applicant: IMGT CO, LTD., Seongnam-si (KR)

(72) Inventors: Hyun Cheol Kim, Seoul (KR); Hyung Won Moon, Seoul (KR); Jin Ho Chang, Seoul (KR)

(73) Assignee: IMGT CO, LTD., Seongnam-si (KR)

( * ) Notice: Subject to any disclaimer, the term of this patent is extended or adjusted under 35 U.S.C. 154(b) by 94 days.

This patent is subject to a terminal disclaimer.

(21) Appl. No.: 15/126,472

(22) PCT Filed: Oct. 13, 2014

(86) PCT No.: PCT/KR2014/009549
§ 371 (c)(1),
(2) Date: Sep. 15, 2016

(87) PCT Pub. No.: WO2015/141917
PCT Pub. Date: Sep. 24, 2015

(65) Prior Publication Data
US 2017/0080114 A1 Mar. 23, 2017

(30) Foreign Application Priority Data
Mar. 19, 2014 (KR) .................. 10-2014-0032057

(51) Int. Cl.
| | | |
|---|---|---|
| A61K 49/22 | (2006.01) | |
| A61K 9/51 | (2006.01) | |
| A61K 9/00 | (2006.01) | |
| A61K 47/69 | (2017.01) | |
| A61P 35/00 | (2006.01) | |

(52) U.S. Cl.
CPC .......... A61K 49/223 (2013.01); A61K 9/0019 (2013.01); A61K 9/5169 (2013.01); A61K 47/6925 (2017.08); A61P 35/00 (2018.01)

(58) Field of Classification Search
CPC .............. A61K 49/223; A61K 47/6925; A61K 9/0019; A61K 9/5169; A61P 35/00
See application file for complete search history.

(56) References Cited

U.S. PATENT DOCUMENTS

| | | | |
|---|---|---|---|
| 4,265,251 A | 5/1981 | Tickner | |
| 4,276,885 A | 7/1981 | Tickner et al. | |
| 2004/0131692 A1* | 7/2004 | Kreuter | A61K 9/5138 |
| | | | 424/499 |
| 2007/0071685 A1* | 3/2007 | Schneider | A61K 41/0028 |
| | | | 424/9.52 |
| 2010/0008863 A1* | 1/2010 | Swenson | A61K 49/223 |
| | | | 424/9.52 |
| 2014/0257100 A1* | 9/2014 | Zheng | A61K 47/22 |
| | | | 600/437 |
| 2015/0343079 A1* | 12/2015 | Kim | A61K 9/127 |
| | | | 424/9.51 |

FOREIGN PATENT DOCUMENTS

| | | | | |
|---|---|---|---|---|
| CN | 101711736 | * | 9/2011 | ............... A61K 9/00 |
| CN | 102525935 | * | 7/2012 | ............... A61K 9/14 |
| EP | 0052575 A2 | | 5/1982 | |
| EP | 0122624 A2 | | 10/1984 | |
| KR | 10-0115739 B1 | | 5/1997 | |
| KR | 10-2005-0096959 A | | 10/2005 | |
| WO | 00/72757 A1 | | 12/2000 | |

OTHER PUBLICATIONS

Lum et al., J. Controlled Release, 2006, 111, p. 128-134.*
Croll et al., Biomacromolecules, 2004, 5, p. 463-473.*
Korean Patent Abstract (in Engiish) of KR Pub No. 10-2005-0096959 A, Pub. Date Oct. 6, 2005, downloaded Aug. 31, 2016 from http://kpa.kipris.or.kr/kpa.
Korean Patent Abstract (in English) of KR Patent. No. 10-0115739 B1, dated May 29, 1997.
European Patent Abstract (in English) of Pub. No. 0052575 A2, Pub. Date May 26, 1982.
European Patent Abstract (in English) of Pub. No. 0122624 A2, Pub. Date Oct. 24, 1984, downloaded Oct. 10, 2016 from http://worldwide.espacenet.com/publicationDetails/.
European Patent Abstract (in German) of Pub. No. 0122624 A2, Pub. Date Oct. 24, 1984, downloaded from http://www.epo.org/.
Huynh, E. et al.; "Porphyrin Shell Microbubbles with Intrinsic Ultrasound and Photoacoustic Properties"; 2012; pp. 6464-16467; J. Am. Chem. Soc.; vol. 134.
Lee, S.H. et al.; P0629 "Ethanol Extract from Lysimachiafoenumgraecum (LFE) Exerts Apoptotic Effects via Regulation of Mitochondrial Pathways in Human Colon Cancer Cells"; KSBB, Abstracts of Current Biotechnology and Bioengineering(XXXII) : Oct. 2013; p. 298; Seoul, Korea.
Kim, G. T. et al.; P0630 "A newly potential as an anti-cancer agent, TJE"; KSBB, Abstracts of Current Biotechnology and Bioengineering(XXXII) : Oct. 2013; p. 298; Seoul, Korea.
Lee, S-H. et al.; P0631 "Hyperglycemic Condition Affects GPx3 mRNA and Protein Expression Levels in HK-2 cells": KSBB, Abstracts of Current Biotechnology and Bioengineering(XXXII) : Oct. 2013; p. 298; Seoul, Korea.

(Continued)

Primary Examiner — Michael G. Hartley
Assistant Examiner — Leah H Schlientz
(74) Attorney, Agent, or Firm — Vorys, Sater, Seymour & Pease LLP; Mih Suhn Koh (57) ABSTRACT

The present invention provides a dual-purpose photoacoustic tomography (PAT)/ultrasound contrast agent comprising: (a) a micro-bubble containing gas and porphyrin therein; and (b) nanoparticles bound on a surface of the micro-bubble and containing a drug. The contrast agent of the present invention can be used in both the ultrasound diagnosis and the photoacoustic image diagnosis, and can significantly increase the accuracy of photoacoustic images.

10 Claims, 8 Drawing Sheets

(56) References Cited

OTHER PUBLICATIONS

Moon, H. et al.; P0632 "Development of Nanoparticle conjugated Ultrasound Contrast Agent for theTumor Theragnosis"; KSBB, Abstracts of Current Biotechnology and Bioengineering(XXXII) : Oct. 2013; p. 298; Seoul, Korea.
WIPO Abstract (in English) of WO Pub. No. 00/72757 A1 , Pub. Date Dec. 7, 2000.
International Search Report, Int'l App. No. PCT/US00/15161 (Int'l Pub. No. WO 00/72757 A1), Pub. dated Dec. 7, 2000.

* cited by examiner

DUAL-PURPOSE PAT/ULTRASOUND CONTRAST AGENT BOUND WITH NANOPARTICLES CONTAINING DRUG AND METHOD FOR PREPARING SAME

CROSS-REFERENCE TO RELATED APPLICATIONS

This application is the national stage for International Patent Cooperation Treaty Application PCT/KR2014/009549, filed Oct. 13, 2014, which claims priority from Korean Patent Application No. 10-2014-0032057, filed Mar. 19, 2014, in the Korean Intellectual Property Office. The entire contents of said applications are incorporated herein by reference for all purposes.

BACKGROUND

Technical Field

The present invention relates to a dual-purpose photoacoustic tomography (PAT)/ultrasound contrast agent bound with nanoparticles containing a drug and a method for preparing the same.

Background Art

Since the exact imaging of biological targets is an important tool for understanding biological phenomena or faultlessly diagnosing various diseases, the current single imaging modality is not suitable. Accordingly, the multi-modality imaging is emerging as an important means, and is becoming a standard method even in the clinical settings. It is possible to overcome many disadvantages of the single imaging modality by combining double- and triple-modality. For example, for early diagnosis of cancers, a technique of simultaneously using the position emission tomography (PET) for allowing highly sensitive functional imaging and computed tomography (CT) capable of providing clear anatomical information has been proposed. Imaging technologies adopting different modalities may be combined, and for example, a combination of magnetic resonance (MR)/optics and PAT/ultrasound may be achieved.

Ultrasound imaging systems have the best advantage in that the systems diagnose disease symptoms in real time, promptly produce the results, and are simpler in configuration and cost less than MRIs and CTs. When an ultrasound contrast agent is administered to a subject, and then ultrasound is applied to the subject, the ultrasound waves are reflected by microbubbles in the contrast agent, making the image of an internal organ more obvious. The ultrasound contrast agent has evolved since Gramiak and Shah found that ultrasound signals were augmented after injecting microbubbles in blood vessels in 1968. Examples of contrast agents known up to now include small air bubbles enclosed by gelatin shell as disclosed in U.S. Pat. No. 4,276,885; small gaseous bodies having polysaccharide solid peripheral walls as disclosed in U.S. Pat. No. 4,265,251; small air bubbles using particulates of solid crystalline compounds (for example: galactose) as disclosed in the European Patent Gazette No. 52575; small air bubbles using fatty acids as disclosed in European Patent Publication No. 0122624; small air bubbles prepared by using fatty acids and surfactants as disclosed in Korean Patent No. 1989-2989, and the like.

The photoacoustic tomography (PAT) technology is an imaging technology which adopts a system of combining high resolution of ultrasound imaging and high contrast ratio of photoimaging and is suitable for the imaging of biological tissues. The technology is so scalable that the technology may also be used to visualize tumors which are located several centimeters below the chest. That is, when laser is irradiated onto a biological tissue, acoustic pressure is generated from a tissue site which acts as a source of generating initial ultrasound waves in the tissue as a short electromagnetic pulse of the laser is absorbed in the biological tissue, the ultrasound waves thus formed reach the surface of the biological tissue, and the PAT imaging visualizes the ultrasound waves. The photoacoustic tomography (PAT) technology also adopts a principle in which cells are stimulated with laser light to allow the cells to emit ultrasound waves, and these ultrasound waves are detected to produce 3D images. The PAT technology, which combines the optical imaging method with the ultrasonic imaging method, thoroughly has noninvasiveness, low costs, portability, excellent contrast ratio, and excellent spatial resolution, and thus, has drawn much attention as a next-generation high resolution medical imaging technology. Currently, the technology fundamentally adopts a system of flashing and irradiating light, and thus has room for much more development in the future in that the imaging depth of the body is limited. However, the technology also supplement other technologies by even using the current imaging depth, and thus, is expected to be utilized in many ways. That is, the above-described PAT technology has an advantage in that the technology may be combined with PET, CT, MR, or ultrasound waves, and the like, and produce the diagnostic results more accurately. In particular, since the ultrasound diagnosis implements images by using ultrasound waves in the same manner as the PAT technology, it is expected that a more exact diagnosis may be enabled when the above-described PAT technology is used with the ultrasound diagnosis. It is essential to develop a contrast agent which may be used simultaneously for the above-described PAT technology and the ultrasound diagnosis, and here, the diagnosis image quality should not deteriorate due to the use of the same contrast agent.

Meanwhile, as the medical technology and the treatment technology are developing, studies have been actively conducted on the development of the theragnosis technology for simultaneously conducting the current diagnosis and treatment. In this regard, attempts have been made to develop a contrast agent capable of simultaneously achieving diagnosis and treatment by using a PAT, CT, MR or ultrasound contrast agent as a carrier to deliver a drug. However, there is a problem in that generally in the structure of a contrast agent used for PAT, CT, MR, or ultrasound diagnosis, the space for carrying a drug is so narrow that it is difficult to load a sufficient drug, and accordingly, it is difficult to enhance the effects of treatment by leaps and bounds.

DISCLOSURE

Technical Problem

The present inventors have intensively studied to develop a contrast agent for diagnosis and treatment, which is capable of simultaneously achieving diagnosis and treatment by being combined with a nano medicine while being able to be used in both the ultrasound diagnosis and the photoacoustic image diagnosis. As a result, the present inventors have found that when porphyrin is included in a microbubble in the form of liposome, which is usually used for ultrasound diagnosis, and nanoparticles containing a drug are combined with the microbubble, the combination may be used in both the ultrasound diagnosis and the photoacoustic image diagnosis, and the accuracy of photoacoustic images may be significantly increased, thereby completing the present invention.

Therefore, an object of the present invention is to provide a contrast agent which may be used in both the ultrasound diagnosis and the photoacoustic image diagnosis.

Further, another object of the present invention is to provide a method for preparing the contrast agent.

The other objects and advantages of the present invention will be more apparent from the following detailed description, claims and drawings of the invention.

Technical Solution

The present invention provides a contrast agent for ultrasound diagnosis and photoacoustic image diagnosis.

The present inventors have intensively studied to develop a contrast agent for diagnosis and treatment, which is capable of simultaneously achieving diagnosis and treatment by combination with a nano medicine while being able to be used in both the ultrasound diagnosis and the photoacoustic image diagnosis. As a result, the present inventors have confirmed that when porphyrin is included in a microbubble in the form of liposome, which is usually used for ultrasound diagnosis, and nanoparticles containing a drug are combined with the microbubble, the combination may be used in both the ultrasound diagnosis and the photoacoustic image diagnosis, and the accuracy of photoacoustic images may be significantly increased.

According to an exemplary embodiment of the present invention, the present invention provides a dual-purpose photoacoustic tomography (PAT)/ultrasound contrast agent comprising: (a) a microbubble containing gas and porphyrin therein; and (b) nanoparticles bound on a surface of the microbubble and containing a drug.

The term 'dual-purpose' used in the present specification may mean that a contrast agent, which is a material of the present invention, may be used in both diagnosis and treatment, and may also be used in both the ultrasound diagnosis and the photoacoustic image diagnosis.

The term 'porphyrin' used in the present specification may mean a compound of the following Chemical Formula 1 or a material which serves the same/similar functions as/to the compound as a material which is a mother nucleus for hemoglobin, chlorophyll, and associated materials thereof.

Chemical Formula 1

The term 'cancer' used in the present specification refers to a complex disease occurring as a result of uninhibited proliferation and disordered growth of transformed cells, and means a solid cancer in the present invention. The solid cancer means all the cancers composed of aggregates except for blood cancer. Examples of the solid cancer include hepatoma, brain tumor, low-grade astrocytoma, high-grade astrocytoma, pituitary adenoma, meningioma, CNS lymphoma, oligodendroglioma, craniopharyngioma, ependymoma, brain stem tumor, head & neck tumor, laryngeal cancer, oropharyngeal cancer, nasal cavity/PNS tumor, nasopharyngeal tumor, salivary gland tumor, hypopharyngeal cancer, thyroid cancer, oral cavity tumor, chest tumor, small cell lung cancer, non-small cell lung cancer (NSCLC), thymoma, mediastinal tumor, esophageal cancer, breast cancer, male breast cancer, abdomen-pelvis tumor, stomach cancer, gall bladder cancer, biliary tract tumor, pancreatic cancer, small intestinal tumor, large intestinal tumor, anal cancer, bladder cancer, renal cell carcinoma, prostatic cancer, cervix cancer, endometrial cancer, ovarian cancer, uterine sarcoma, and skin cancer, but are not limited thereto.

According to an exemplary embodiment of the present invention, the drug of the present invention may be a hardly soluble organic drug.

The term 'organic' may be understood to mean a material including carbon in the molecule, and the term 'hardly soluble' may mean that a pharmacologically active preparation is not dissolved in an aqueous solution (for example: water, physiological saline, an injectable dextrose solution, and the like).

The meaning of the term 'hardly soluble' will be described in more detail based on solubility as follows. The USP/NF generally expresses the solubility as the volume of a solvent required to dissolve 1 g of a drug at a specific temperature (for example: 1 g of aspirin in 300 ml of H2O and 5 ml of ethanol at 25° C.). Other references may describe the solubility by using more subjective terms such as those given in the following Table 1 suggested in the literature [see; Remington's Pharmaceutical Sciences, Mack Publishing Co., Easton, Pa., latest edition].

TABLE 1

| Technical term | Parts by weight of a required solvent per 1 part by weight of a solute |
|---|---|
| Very highly soluble | <1 |
| Highly soluble | 1 to 10 |
| Soluble | 10 to 30 |
| Insufficiently soluble | 30 to 100 |
| Poorly soluble | 100 to 1,000 |
| Very poorly soluble | 1,000 to 10,000 |
| Practically insoluble or insoluble | >10,000 |

Therefore, the term "hardly soluble" of the present invention may include a pharmacologically active preparation which belongs to the four lower solubility categories in Table 1, that is, "Insufficiently soluble", "Poorly soluble", "Very poorly soluble", and "Practically insoluble or insoluble" when water is used as a solvent.

The hardly soluble material may include a pharmacologically active preparation, a diagnostic preparation, a nutrient preparation, and the like, and a hardly soluble material as the pharmacologically active preparation may include compounds listed in "Therapeutic Category and Biological Activity Index" of The Merck Index (12th Ed., 1996).

According to an exemplary embodiment of the present invention, the drug of the present invention may be an anticancer drug in hardly soluble organic drugs, and examples thereof include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol, beta-2-deoxythioguanosine, bisantrene HCl, bleomycin sulfate, busulfan, buthionine sulfoximine, BWA 773U82, BW 502U83/HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, dedatrexate, edelfosine, eplolnitin, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol™, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alpha, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extract of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor (TNF), uracil mustard, vinblastine sulfate, vincristine sulfate, vindesine, vinorelbine, vinzolidine, Yoshi 864, zorubicin, mixtures thereof, and the like, but are not limited thereto.

According to an exemplary embodiment of the present invention, the nanoparticle of the present invention may include albumin to form self-aggregates.

As the nanoparticle, a flocculating protein may be used, and preferably, it is possible to use a publicly-known albumin which may maintain a flocculating structure to stably transfer a drug while circulating in the blood for a long period of time, and is cancer-targeting.

The term 'self-aggregates' used in the present specification may mean a material which is not collected by an external force, but forms aggregates by a peculiar intermolecular attractive force or repulsive force which the material includes.

According to an exemplary embodiment of the present invention, the size of the nanoparticles in the present invention is important. This is because nanoparticles having a size of several tens to several hundreds of nanometers through loose vascular tissues formed by the cancer tissue may be accumulated around cancer tissues, the infiltrated nano carrier may remain in the cancer tissues without being discharged due to a lymphatic vessel which fails to properly function around the cancer tissues, this phenomenon refers to an enhanced permeability and retention (EPR) effect, and particles having a diameter of less than 200 nm generally exhibit the best efficiency.

Accordingly, the size of the nanoparticles of the present invention may be preferably 10 to 500 nm, more preferably 50 to 400 nm, and most preferably 100 to 300 nm.

According to an exemplary embodiment of the present invention, the nanoparticle of the present invention may be bound to the microbubble through a linker or an activated reactive group on the surface of the microbubble. The reactive group may be a thiol group or an amine group, or the linker may be a compound including the reactive group.

More specifically, the microbubble and the nanoparticle may be amide-bonded to each other. The bond may be formed via amide bond occurring between a carboxyl group in the microbubble and a plurality of amine groups included in the albumin.

According to an exemplary embodiment of the present invention, the microbubble of the present invention may be preferably a gas-filled microsphere, a gas-filled liposome or a gas-forming emulsion, and most preferably a gas-filled liposome.

The liposome is formed by an amphiphilic compound including phospholipids. The amphiphilic compounds are typically arranged at the interface between organic solvents which are essentially water-insoluble with an aqueous medium to stabilize emulsified solvent microbubbles. The amphiphilic compound includes a compound including a molecule having a hydrophilic polar head portion (for example: a polar or ionic group) capable of being reacted with an aqueous medium and for example, a hydrophobic organic tail portion (for example: a hydrocarbon chain) capable of being reacted with an organic solvent. The amphiphilic compound is a compound which may stabilize a mixture of materials which may not be usually mixed by other methods, such as a mixture of two non-miscible liquids (for example: water and oil), a mixture of liquid and gas (for example: gas microbubbles in water) or a mixture of liquid and insoluble particles (for example: metal nanoparticles in water). In particular, in the present invention, an inert gas and water are injected into a phospholipid thin film, and then ultrasound treatment is performed thereon to form a liposome filled with the inert gas therein.

The amphiphilic phospholipid compound contains at least one phosphate group and at least one, preferably two, lipophilic long-chain hydrocarbon groups.

As the amphiphilic phospholipid, a publicly-known compound may be used, and examples thereof include diphytanoylphosphatidylcholine, 1,2-dipalmitoyl-sn-glycero-3-phosphocholine (DPPC), 1,2-diheptanoyl-sn-glycero-3-phosphocholine (DHPC), 1,2-dihexanoyl-sn-glycero-3-phosphoethanolamine (DHPE), 1,2-dimyristoyl-sn-glycero-3-phosphocholine (DMPC), 1,2-DiODodecyl-sn-glycero-3-phosphocholine (DIODPC), dimyristoyl phophatidylserine (DMPS), dimyristoyl phosphatidylglycerol, dilauryl phosphatidycholine (DLPC), 1,2-dimyristoyl-sn-glycero-3-phosphoethanolamine (DMPE), 1,2-dimyristoyl-sn-glycero-3-[phospho-rac-(1-glycerol)] (DMPG), 1-myristoyl-2-hydroxy-sn-glycero-3-phosphocholine (Lyso PC), 1-oleoyl-2-hydroxy-sn-glycero-3-phosphoethanolamine (Lyso PE), 1,2-didecanoyl-sn-glycero-3-phosphocholine (DDPC), 1,2-dierucoyl-sn-glycero-3-phosphate (sodium salt) (DEPA-NA), 1,2-erucoyl-sn-glycero-3-phosphocholine (DEPC), 1,2-dierucoyl-sn-glycero-3-phosphoethanolamine (DEPE), 1,2-linoleoyl-sn-glycero-3-phosphocholine (DLOPC), 1,2- dilauroyl-sn-glycero-3-phosphate (sodium salt) (DLPA-NA), 1,2-dilauroyl-sn-glycero-3-phosphoethanolamine (DLPE), 1,2-dilauroyl-sn-glycero-3-phosphoserine (sodium salt) (DLPS-NA), 1,2-dimyristoyl-sn-glycero-3-phosphate (sodium salt) (DMPA-NA), 1,2-dimyristoyl-sn-glycero-3-phosphoserine (sodium salt) (DMPS-NA), 1,2-dioleoyl-sn-glycero-3-phosphate (sodium salt) (DOPA-NA), 1,2-oleoyl-sn-glycero-3-phosphocholine (DOPC), 1,2-dioleoyl-sn-glycero-3-phosphoethanolamine (DOPE), 1,2-dioleoyl-sn-glycero-3-phosphoserine (sodium salt) (DOPS-NA), 1,2-dipalmitoyl-sn-glycero-3-phosphate (sodium salt) (DPPA-NA), 1,2-dipalmitoyl-sn-glycero-3-phosphoethanolamine (DPPE), 1,2-dipalmitoyl-sn-glycero-3-phosphoserine (sodium salt) (DPPS-NA), 1,2-distearoyl-sn-glycero-3-phosphate (sodium salt) (DSPA-NA), 1,2-distearoyl-sn-glycero-3-phosphocholine (DSPC), 1,2-diostearpyl-sn-glycero-3-phosphoethanolamine (DSPE), 1-myristoyl, 2-stearoyl-sn-glycero 3-phosphocholine (MSPC), 1-palmitoyl, 2-myristoyl-sn-glycero 3-phosphocholine (PMPC), 1-palmitoyl, 2-oleoyl-sn-glycero 3-phosphocholine (POPC), 1-palmitoyl-2-oleoyl-sn-glycero-3-phosphoethanolamine (POPE), 1-palmitoyl, 2-stearoyl-sn-glycero 3-phosphocholine (PSPC), 1-stearoyl, 2-myristoyl-sn-glycero 3-phosphocholine (SMPC), 1-stearoyl, 2-palmitoyl-sn-glycero 3-phosphocholine (SOPC), and 1-stearoyl, 2-palmitoyl-sn-glycero 3-phosphocholine (SPPC).

Further, as the amphiphilic phospholipid compound, a modified phospholipid compound may be used. As an example of the modified phospholipid, examples of the modified phospholipid to which polyethylene glycol (PEG) is added include phosphatidylethanolamine (DMPE-PEG) or phosphoethanolamine (DSPE-PEG) modified with polyethylene glycol (PEG), and the like.

According to an exemplary embodiment of the present invention, the amphiphilic phospholipid compound used in the present invention may include N-hydroxy succinimide (NHS) for forming an amide bond.

The present invention may further include an additional amphiphilic material in addition to the amphiphilic compound, and examples thereof include lysolipid, stearic acid, polyethyleneglycol, polyoxyethylene fatty acid ester, polyoxyethylene fatty acid stearate, polyoxyethylene fatty alcohol, and the like.

According to an exemplary embodiment of the present invention, as the gas to be internally filled in the liposome of the present invention, a publicly-known gas may be used without limitation, and as an example, carbon dioxide, helium, nitrogen, argon, sulfur hexafluoride, and perfluorinated gases may be used. As the gas, a fluoride including fluorine gas is preferred, and examples thereof include perfluoropropane (C3F8), sulfur hexafluoride (SF6), perfluoropentane, decafluorobutane, and perfluorohexane.

According to an exemplary embodiment of the present invention, the microbubbles of the present invention may have a diameter of preferably 0.1 to 20 μm, and most preferably 1 to 10 μm.

The contrast agent of the present invention may be parenterally administered, and in the case of a parenteral administration, the contrast agent may be administered by intravenous injection, subcutaneous injection, intramuscular injection, intraperitoneal injection, transdermal administration, and the like.

A suitable administration amount of the contrast agent of the present invention may vary depending on factors, such as formulation method, administration method, age, weight, sex or disease condition of a patient, diet, administration time, administration route, excretion rate and response sensitivity. Meanwhile, the administration amount of the contrast agent of the present invention may be preferably 0.001 to 100 mg/kg (body weight).

According to another exemplary embodiment of the present invention, the present invention provides a method for preparing a dual-purpose photoacoustic tomography (PAT)/ultrasound contrast agent, the method comprising: (a) preparing each of a microbubble including porphyrin and a nanoparticle containing a drug; and (b) mixing the nanoparticle and the microbubble at a predetermined ratio in water to be reacted.

The method for preparing the microbubble may include: mixing an emulsifier, porphyrin-lipid, lipid, and lipid including NHS with an organic solvent to form a lipid thin film; and putting the lipid thin film into water to hydrate the lipid thin film, and performing an ultrasound treatment thereon while injecting gas thereinto and maintaining high pressure.

In the forming of the lipid thin film, the emulsifier: porphyrin-lipid:lipid:lipid including NHS may be mixed at a molar ratio of 5 to 10:15 to 30:60 to 75:15 to 30.

As a method of putting the lipid thin film into water to hydrate the lipid thin film and filling a gas, a publicly-known method may be used, and for example, an ultrasound treatment may be performed by putting a mixed solution of water, glycol, and glycerin into a container including a lipid thin film to dissolve the lipid thin film while maintaining a temperature of 55 to 60° C., and putting a gas thereinto at 200 kPa, or ultrasound wave and mechanical agitation methods may be used in combination.

The preparing of the nanoparticle containing a drug includes dissolving albumin in water, and then injecting a drug thereinto to prepare a mixture, and adjusting a pH of the mixture to 7 to 10, preferably 8.0 to 8.5, and then adding alcohol dropwise thereto, and the albumin may form self-aggregates by the steps.

Advantageous Effects

The features and advantages of the present invention will be summarized as follows:

The present invention provides a dual-purpose photoacoustic tomography (PAT)/ultrasound contrast agent comprising: (a) a microbubble containing gas and porphyrin therein; and (b) nanoparticles bound on a surface of the microbubble and containing a drug.

The contrast agent of the present invention has an advantage in that the contrast agent may be used in both the ultrasound diagnosis and the photoacoustic image diagnosis, and the accuracy of photoacoustic images may be significantly increased.

BRIEF DESCRIPTION OF THE DRAWINGS

The lower drawing in FIG. 4 illustrates data indicating that photoacoustic signals are amplified in porphyrin MBs-NPs compared to porphysome.

DETAILED DESCRIPTION

Best Mode

Hereinafter, the present invention will be described in more detail through the Examples. These Examples are provided only for more specifically describing the present invention, and it will be obvious to a person with ordinary skill in the art to which the present invention pertains that the scope of the present invention is not limited by these Examples according to the gist of the present invention.

EXAMPLES

Throughout the present specification, unless otherwise specifically stated, for "%" used in order to indicate the concentration of a specific material, the solid/solid is (wt/wt) %, the solid/liquid is (wt/vol) %, and the liquid/liquid is (vol/vol) %.

PREPARATION EXAMPLES

Preparation Example 1: Preparation of Lipid-Containing Porphyrin

A preparation was made by an acylation reaction of porphyrin-lipidsms lysophosphatidylcholine which is a sub-unit of a porphyrin microbubble with pyrophephorbide. First, 100 nmol of 1-palmitoyl-2-hydroxyl-sn-glycero-3-phosphocholine, 50 nmol of pyropheophorbide, 50 nmol of 1-ethyl-3-(3-dimethylaminopropyl)carbodiimide, 25 nmol of 4-(dimethylamino) pyridine, and 50 µL of N,N-diisopropylethylamine were dissolved in 10 mL of anhydrous dichloromethane, and then reacted under an argon environment for 48 hours in a state where light was blocked at normal temperature. Thereafter, the residue left by evaporating all the solvents was purified by thin layer chromatography (20×20 cm pre-coated silica gel plate with fluorescent indicator, a thickness of 1.5 mm), and in this case, the residue was purified by extraction when the retardation factor (Rf) of the thin layer chromatography was 0.4 as a main band. For the purification method, the chromatography was performed by using diol modified silica, and then impurities were removed by using dichloromethane containing 2% and 5% methanols, and purification was performed by using dichloromethane containing 8% methanol. The purified pyropheophrobide-lipid was aliquoted at a concentration of 1 µmol, dried by flowing nitrogen gas, and stored at −20° C. under the argon environment. The purity of the extracted porphyrin-lipid was analyzed by high-performance liquid chromatography and mass spectrometry (conditions: Phenomenex Jupiter C4 column, 0.4 mL/min flow from 25% to 95% acetonitrile followed by holding 0.1% trifluoroacetic acid, compound eluted at 32 min, observed mass: 1013.1).

Preparation Example 2: Preparation of Microbubbles Including Porphyrin 1,2-disteraoyl-sn-glycero-3-phosphocholine (DSPC), DSPE-PEG2000-NHS (1,2-dioleoyl-sn-glycero-3-phosphoethanolamine-n-[poly(ethyleneglycol)] 2000-N-hydroxysuccinimide), and a lipid containing porphyrin (porphyrin-lipid) as the lipids, and polyoxyethylene 40 stearate (POE40s) as an emulsifier were mixed at a molar ratio of 50:15:15:1 and dissolved in chloroform, and then the chloroform was completely evaporated by using a rotary evaporator to form a lipid thin film. Subsequently, distilled water, propylene glycol, and glycerin were mixed at a ratio of 8:1:1, and then the resulting mixture was added to the lipid thin film. The lipid was dissolved while the temperature was maintained at 55 to 60° C. SF6 or C3F8 gas was put into a container containing the mixed solution, the container was filled with the gas at 200 kPa, and then microbubbles (porphyrin-MBs) were prepared through sonication and mechanical agitation.

Preparation Example 3: Preparation of Nanoparticles (HSA-NPs)

40 mg of a human serum albumin (HSA) was dissolved in 1 mL of distilled water, and then 100 to 200 µL t of paclitaxel (5 mg/mL) was mixed in a vial in which HSA was dissolved. The pH of the mixed solution was titrated to 8.0 to 8.5 by using KOH or NaOH, and then 3 to 6 mL of ethanol was titrated to the mixed solution at a rate of 1 mL/min. 8%-glutaraldehyde, which is a crosslinking agent, was put thereinto and the reaction was performed until the HSA was aggregated and the mixed solution became turbid. Subsequently, the solution left by completely evaporating ethanol was centrifuged under the conditions of 12,000 rpm, 4° C., and 10 minutes. The other aliquots were removed except for the settled pellet, and HSA and paclitaxel, which had not been particularized, were removed, and then washed with distilled water. Centrifugation was performed under the conditions of 3,000 rpm, 4° C., and 5 min to remove micro-sized particles and extract HSA nanoparticles (HSA-NPs) loaded with paclitaxel having a size of 100 to 200 nm.

Preparation Example 4: Binding of Microbubbles and Nanoparticles

HSA nanoparticles and microbubbles including porphyrin were mixed at a molar ratio of 1:0.5 to 2 in a combined reactor at normal temperature for 2 hours to bind nanoparticles to microbubbles through amide bonds. The unbound HSA nanoparticles were removed by centrifugation to completely prepare the contrast agent (porphyrin-MBs-NPs) in Example 1. For reference, when in order to complement the lost NHS during the preparation of microbubbles, EDC and NHS were sufficiently added in advance to perform a reaction, and the residual EDC and NHS were washed by a centrifuge, the binding efficiency may be further enhanced.

Comparative Example 1

Microbubbles (porphyrin-MBs) including porphyrin prepared by the method in the Preparation Examples were used as Comparative Example 1 (nanoparticles were not bonded to microbubbles).

EXPERIMENTAL EXAMPLES

Experimental Methods

Experimental Method 1: Ultrasound Scanning

For the ultrasound imaging, 0.5 mg/mL of porphyrin MBs prepared and porphyrin MBs-NPs were diluted at 1/50, the dilution was put into a phantom manufactured with an agarose gel, and then images were produced by a commercially available ultrasound diagnostic system using a transducer of 2 to 5 MHz. In this case, the diagnostic mode used was a harmonic mode, components from the ultrasound contrast agent were detected and the diagnosis was conducted by setting the intensity of the emitted ultrasound waves to 0.1 mechanical index.

Experimental Method 2: Photoacoustic Image Scanning

For the photoacoustic imaging, porphyrin MBs and porphyrin MBs-NPs at the same concentration as in the ultrasound imaging experiment were put into a tube and data were obtained by irradiating laser with a wavelength of 700 nm, and images were reconstructed by using a matlab program.

Experimental Method 3: Analysis Method of Anticancer Effects in Cells

About 20,000 cells were seeded onto a 96-well plate, and then 400 nM, which is the same amount based on paclitaxel, was added thereto, and then the cells were divided into a group which was contrasted with ultrasound waves and a group which was not contrasted with ultrasound waves, and a control which was not subjected to any treatment, free-MBs to which PTX-NPs were not bound, nanoparticles (PTX-NPs) containing 400 nM of PTX, and nanoparticles to which PTX-NPs containing 400 nM of PTX were bound were used to verify the apoptotic effects over time for each group. The degree of apoptosis was quantitatively analyzed by using an MTT assay.

Experimental Method 4: Analysis Method of Infiltration Effects in Cancer Cells

An experiment was performed under the same conditions as in the photoacoustic image experiment by using Balb/C nude mice xenografted with MDA-MB-231 cells. First, the tumor before the injection was visualized, 200 µL of porphyrin MBs at 0.5 mg/mL was injected through the tail vein injection, and then images were obtained.

Figure 1:
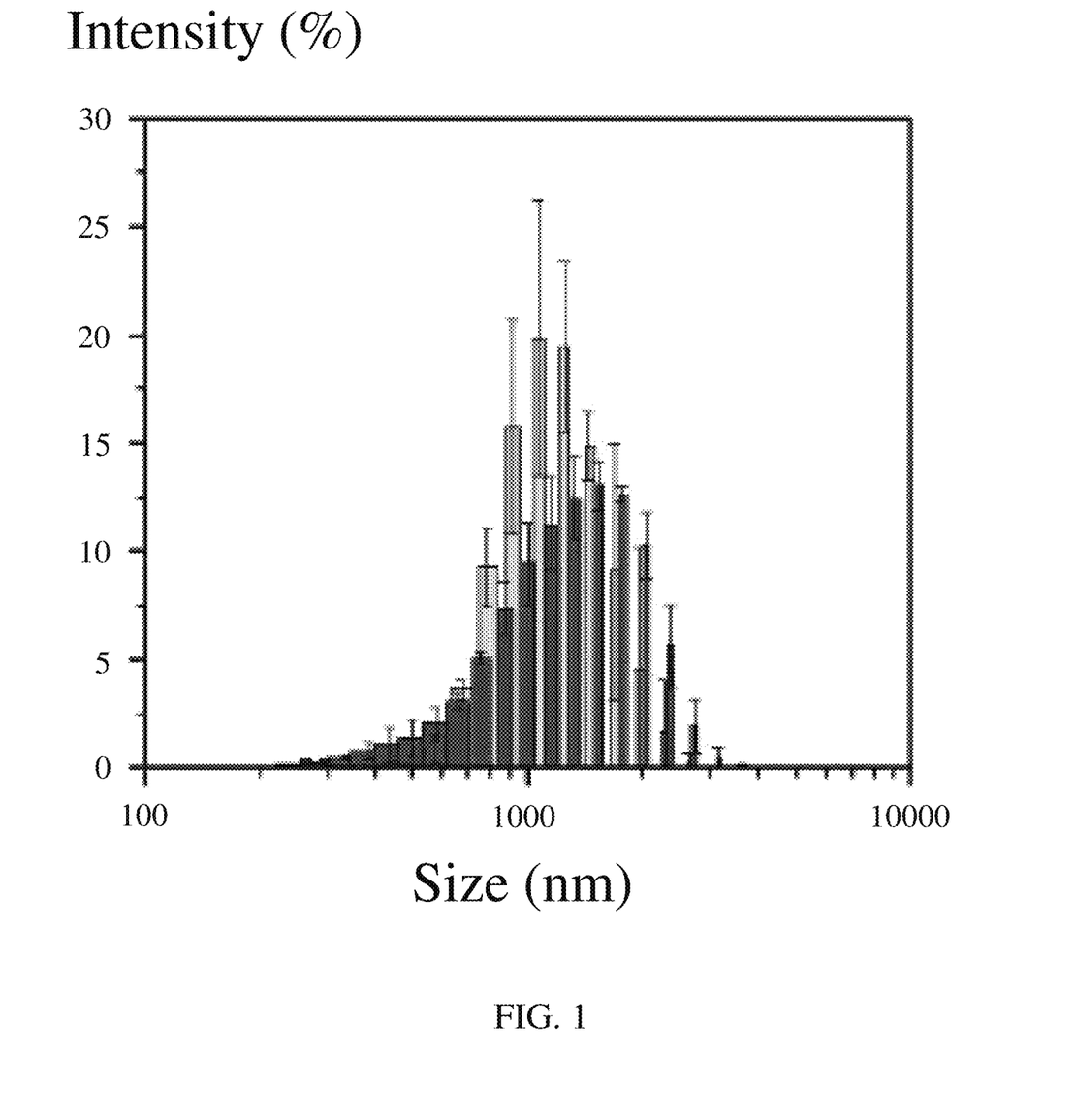
FIG. 1 illustrates data meaning that human serum albumin nanoparticles (PTX-NPs) containing an anticancer agent (paclitaxel: PTX) are bound on porphyrin microbubbles (porphyrin-MB s).
Figure 2:
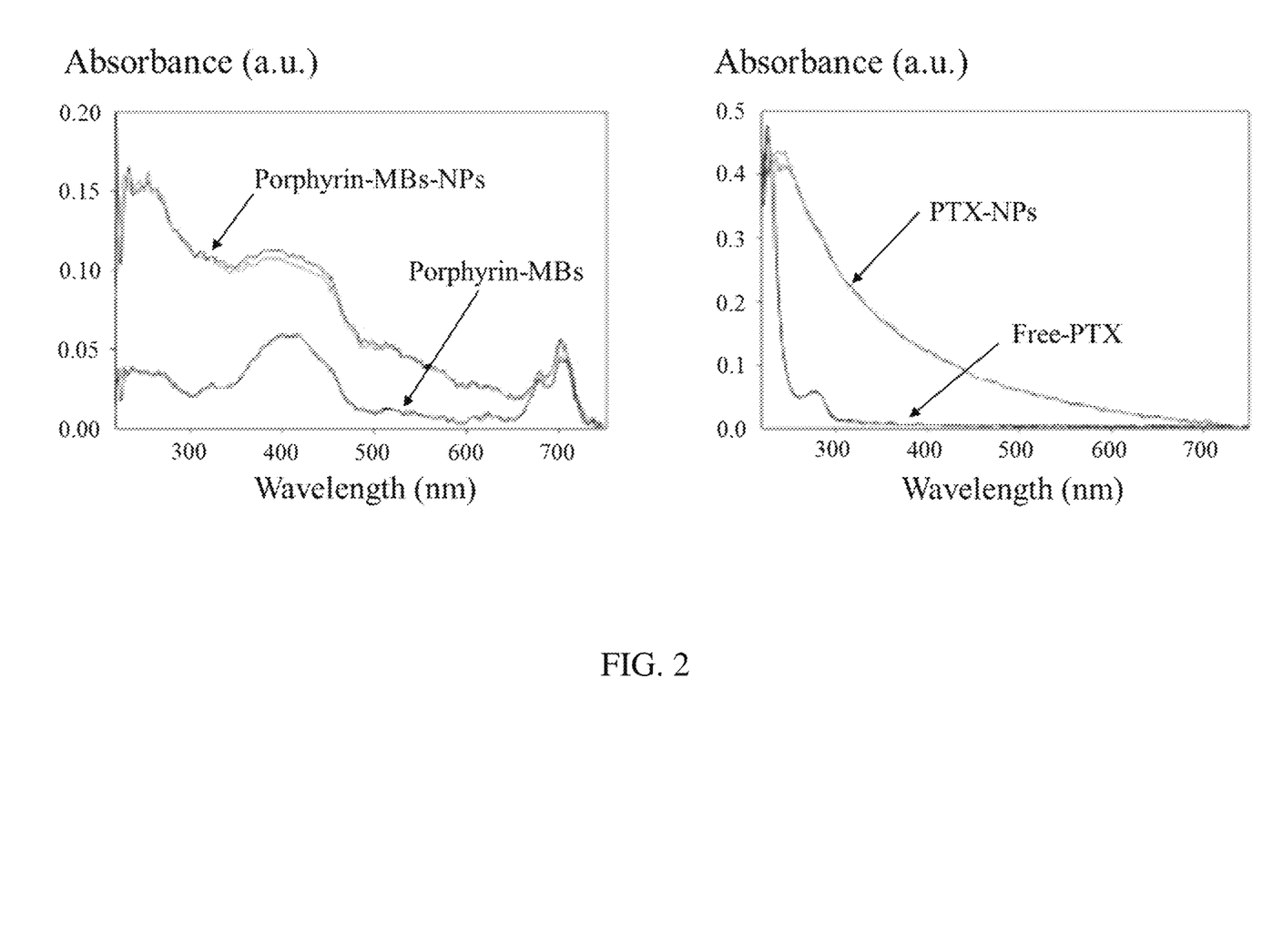
FIG. 2 illustrates the result of analyzing the presence and absence of bonding of porphyrin-MBs-NPs through UV-vis spectroscopy.

Experimental Example 1: Confirmation of Bonding State of Microbubbles and Nanoparticles FIG. 1 illustrates data meaning that human serum albumin nanoparticles (PTX-NPs) containing an anticancer agent (paclitaxel: PTX) are bound on porphyrin microbubbles (porphyrin-MBs). Referring to FIG. 1, it can be seen that the data exhibit the change in size before and after PTX-NPs were bound to porphyrin-MBs-NPs, and as a result of binding PTX-NPs showing a size of 190.1±52.6 nm to porphyrin-MBs showing a size distribution of 1.1±1.2 µm, a size distribution of 1.6±2.5 µm was exhibited, and the peak was moved. FIG. 2 is a result of analyzing whether porphyrin-MBs-NPs were bound by UV-vis spectroscopy, and the data on the left side indicate the measurement of porphyrin-MBs and porphyrin-MBs-NPs. It can be seen that in the case of porphyrin-MBs, only a porphyrin peak exhibiting a wavelength of 700 nm was detected, but in the case of bonding of PTX-NPs, PTX-NPs with a wavelength of 227 nm were together detected, and thus, nanoparticles (PTX-NPs) containing an anticancer agent for treatment were bound. The data on the right side in FIG. 2 indicate data verifying whether the anticancer agent (paclitaxel) was load into the inside of nanoparticles, and it can be seen that the UV absorption peak (227 nm) of pure paclitaxel was detected at the PTX-NPs, and thus the anticancer agent (paclitaxel) was effectively loaded into nanoparticles.

Experimental Example 2: Verification of Ultrasound Waves and PAT Images

Figure 3:
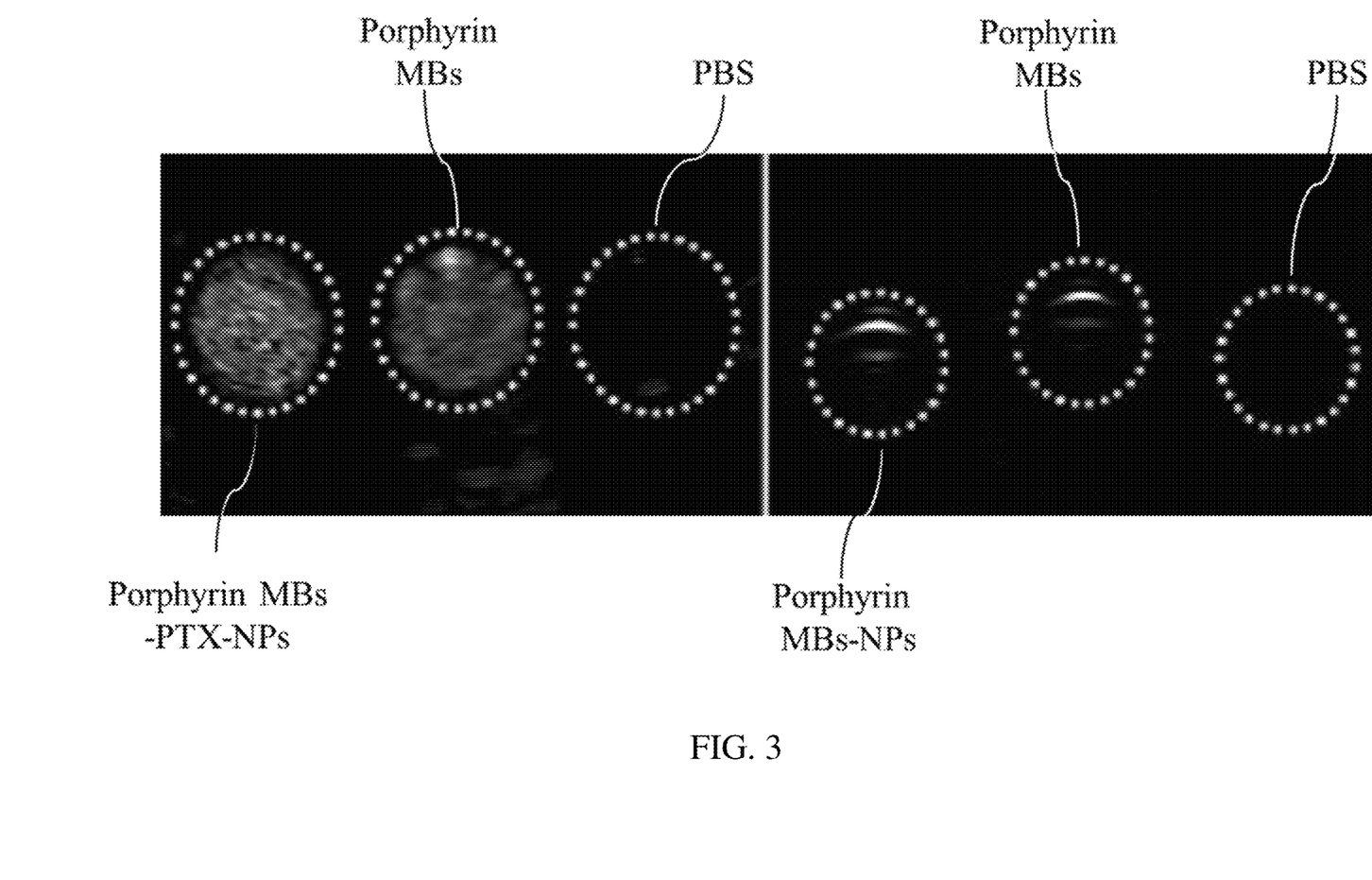
FIG. 3 illustrates a result of verifying ultrasound and photoacoustic images of porphyrin-MBs-NPs and porphyrin MBs developed in the present invention.

FIG. 3 illustrates a result of verifying ultrasound and photoacoustic images of porphyrin-MBs-NPs and porphyrin MBs developed in the present invention, and it was found that the effects of images had not be reduced by bonding to PTX-NPs. The ultrasound image on the left side in FIG. 3 is a result obtained by detecting ultrasound images by using a transducer of 2 to 5 MHz for each agent diluted at 1/50 (concentration of porphyrin MBsNPs and porphysome: 10 µg/mL) with a phantom manufactured with Agarose and using a commercially available ultrasound diagnostic system to detect ultrasound images, and detecting harmonic components from porphyrin MBs-NPs when the diagnostic mode used in this case was a harmonic mode. For the photoacoustic image on the right side in FIG. 3, each agent diluted at 1/50 (concentration of porphyrin MBs-Nps and porphysome: 10 µg/mL) was injected into the tube, and then the image was detected by using laser with a wavelength of 700 nm. It was confirmed that for the ultrasound and photoacoustic images, images were not detected without any agent by using a phosphate buffer saline (PBS) as a control.

Figure 4:
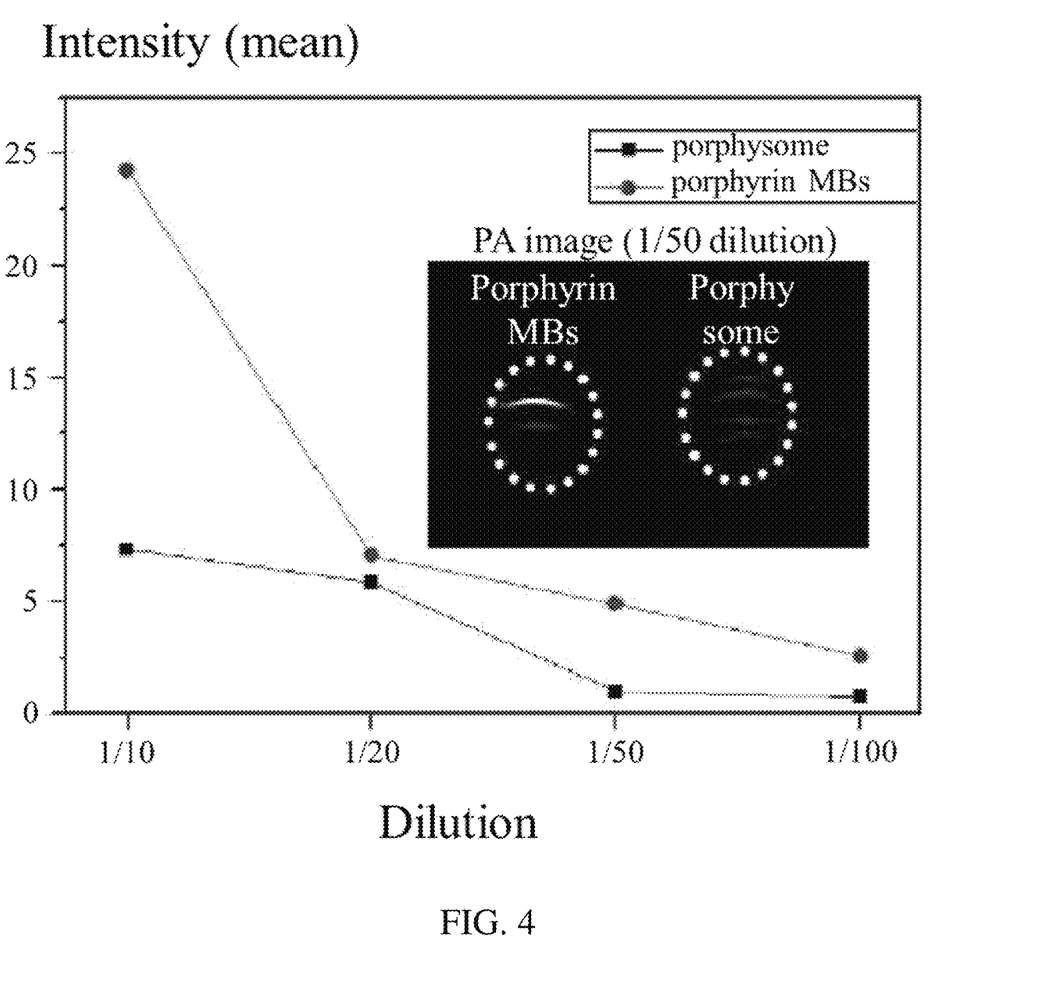

Experimental Example 3: Confirmation of Amplified State of Photoacoustic Signals FIG. 4 illustrates data indicating that photoacoustic signals are amplified in porphyrin MBs-NPs compared to porphysome. When images were detected at each dilution of 1/10, 1/20, 1/50, and 1/100 times (concentration of original solutions: 0.5 mg/mL), it was exhibited that signals of porphyrin MBs were increased as microbubbles were formed, and in the images at 1/50-time dilution, a clear difference in intensity was also exhibited. Images were obtained by the same method as when the photoacoustic images in Experimental Method 2 were scanned, and then the intensity of the images was detected by using a matlab program.

Figure 5:
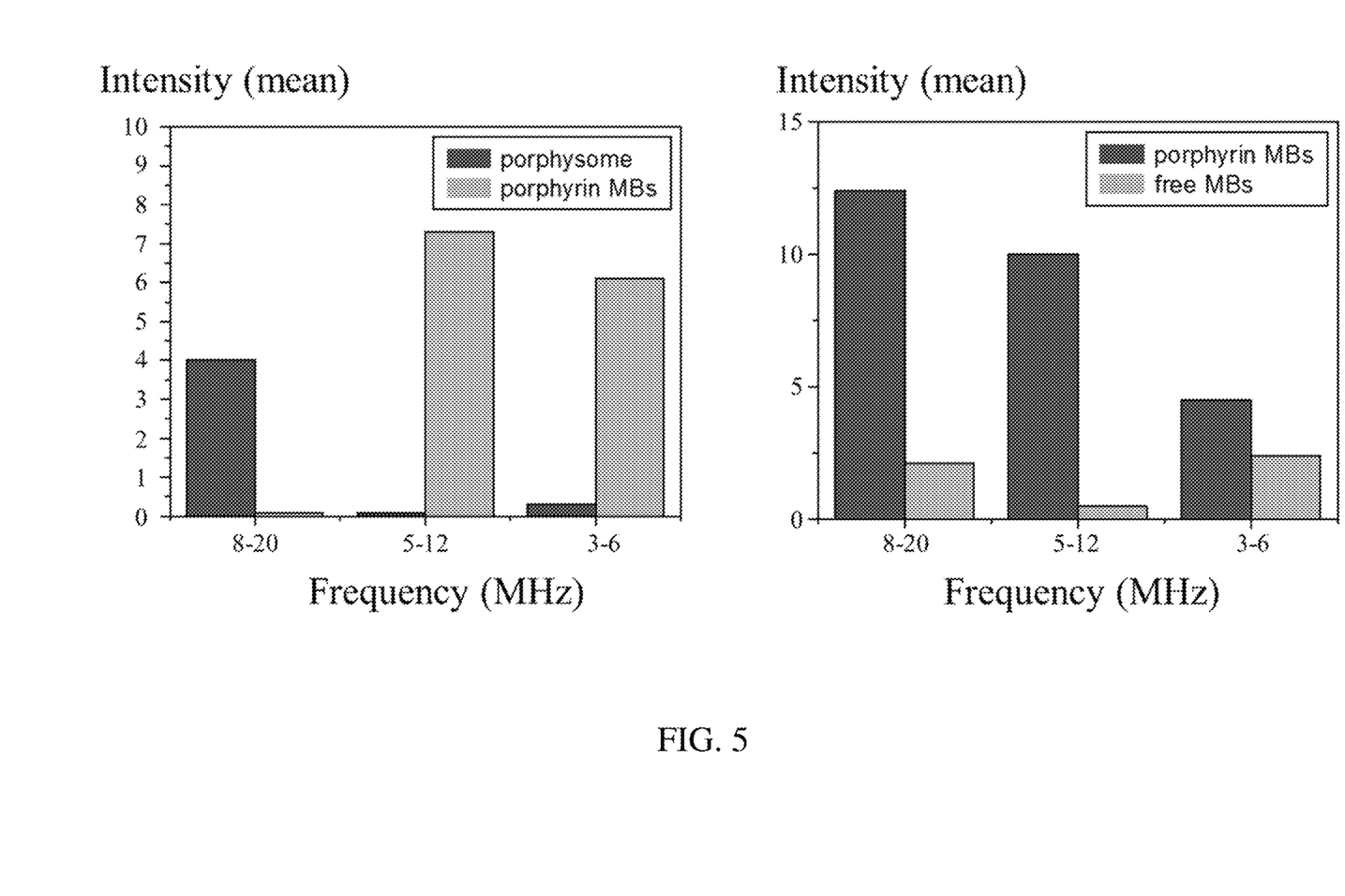
FIG. 5 illustrates an experimental result of analyzing the intensity of detected signals according to the frequency band of a transducer used in detecting acoustic signals in the present experiment.

Experimental Example 4: Analysis of Intensity of Signals According to Frequency Band FIG. 5 illustrates an experiment of analyzing the intensity of signals detected according to the frequency band of a transducer used when acoustic signals are detected, and the graph on the left side illustrates data comparing porphyrin MBS with porphysome. When the intensity of signals of the porphyrin MBs was compared with signals of porphysome at low wavelengths, the intensity was increased by about 100 times in a transducer of 5 to 12 MHz and increased by about 60 times in a transducer of 2 to 5 MHz. In the present experiment, signals were detected by using a transducer having each frequency band using porphysome, porphyrin MBs and free MBs (microbubbles containing no porphyrin) diluted at 1/50 times in the same manner as in the photoacoustic image experiment in Experimental Method 2. For the obtained signals, the intensity each obtained was verified by using a matlab program.

Figure 6:
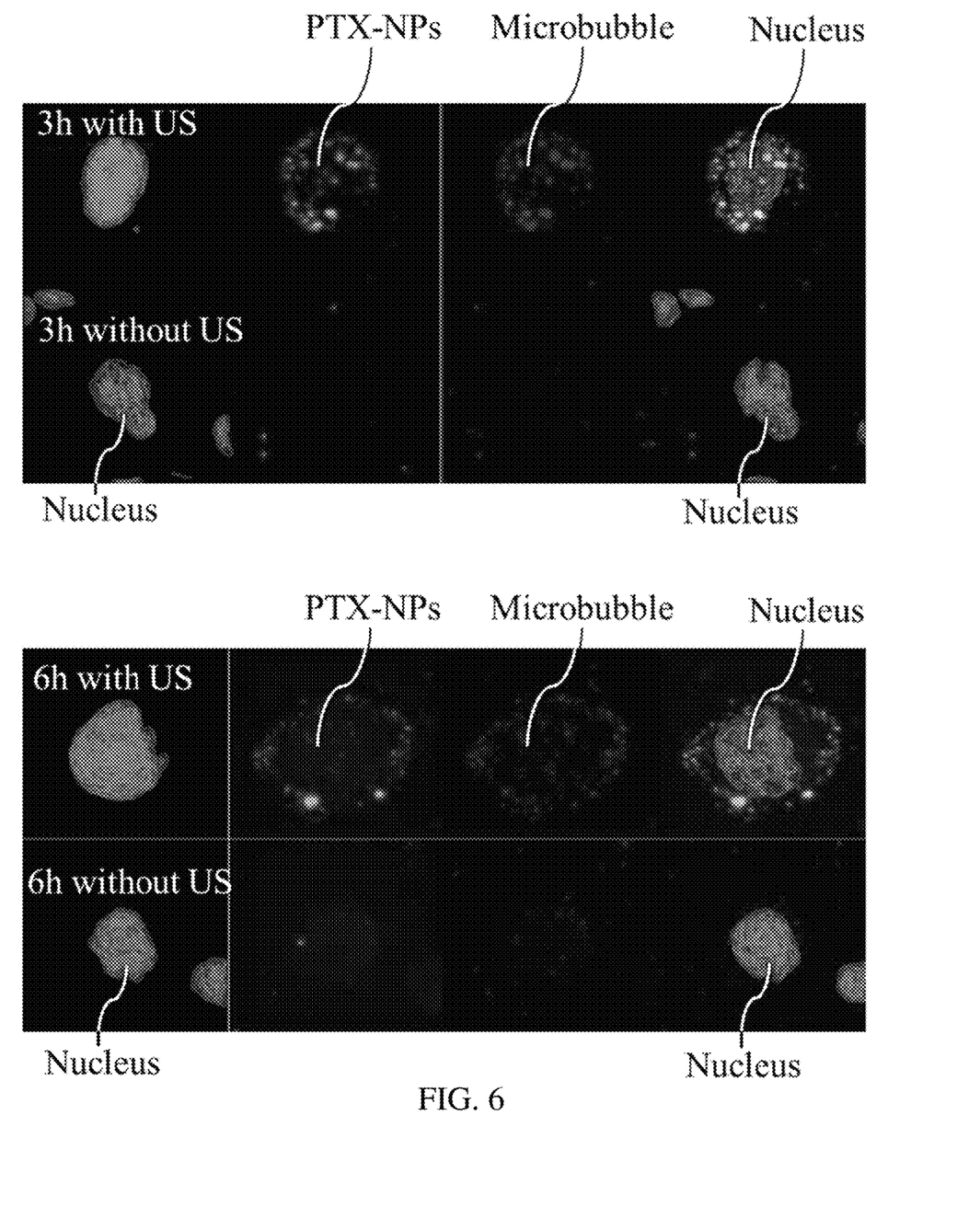
FIG. 6 illustrates data of analyzing the effects of infiltrating the prepared agent into MDA-MB-231 cells.

Experimental Example 5: Analysis of Infiltration Effects of Contrast Agent into Cells FIG. 6 illustrate data of analyzing the effects of infiltrating the prepared agent into MDA-MB-231 cells, the fluorescence of the green color was detected by preparing particles using a bovine serum albumin in which FITC was bound to PTX-NPs, and the fluorescence was detected by loading the microbubbles with DiI-c18 (red) which is a lipophilic fluorescent material Here, as compared with a group contrasted with ultrasound waves, the infiltration effects into cells were increased due to the cavitation effects resulting from the resonance of ultrasound waves and microbubbles as the ultrasound wave was applied. The scanning of cell images was performed by using a confocal microscopy.

Experimental Example 6: Analysis of Anticancer Effects

Figure 7:
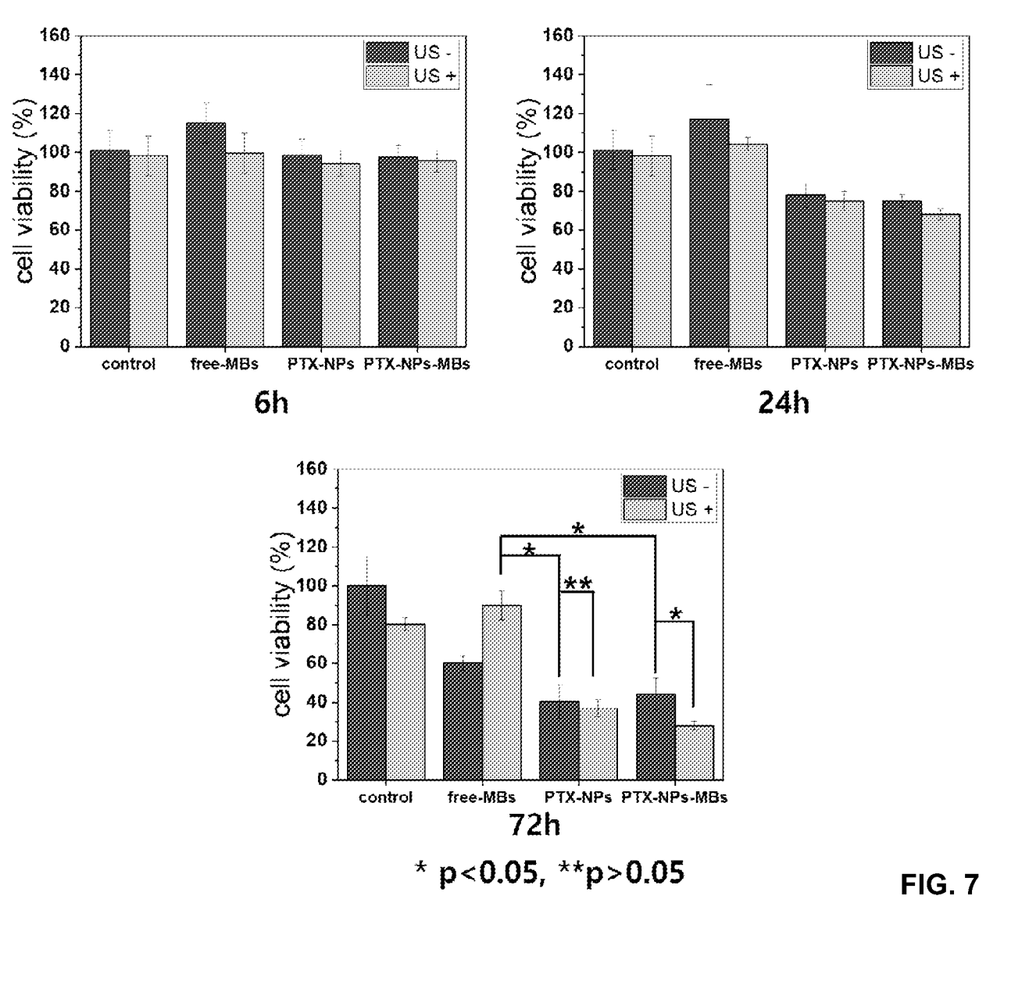
FIG. 7 illustrates data of analyzing the anticancer effects on cells over time.

FIG. 7 illustrates data that anticancer effect in cells was analyzed over time, and the experiments were conducted in the groups in which free porphyrin MBs, PTX-NPs, and porphyrin MBs-NPs (PTX-NPs-MBs) were contrasted and not contrasted with ultrasound (US) waves by using no-treatment group as a control. PTX-NPs and PTX-NPs-MBs, which are groups containing PTX, exhibited anticancer effects of 60% or more after 72 hours, and in particular, the group contrasted with US (US+) exhibited that anticancer effects were increased due to the cavitation effects of microbubbles and ultrasound waves in the PTX-NPs-MBs group containing microbubbles (see Experimental Method 3).

The results of the present experiment are as follows.

(6 h: control; 100.00±11.11%, 97.15±12.43% (US+), free-microbubble; 109.40±12.28%, 94.64±15.11% (US+), PTX-NPs; 98.51±9.69%, 93.31±7.16% (US+), PTX-NPs-MBs; 96.90±8.93%, 92.32±7.16% (US+), 24 h control; 100±9.99%, 97.81±10.08% (US+), free-microbubble; 116.51±19.82%, 101.80±3.56 (US+), PTX-NPs; 85.04±8.60%, 83.80±6.83% (US+), PTX-NPs-MBs; 80.99±2.35%, 75.70±1.64% (US+), and 72 h: control; 100.00±16.66%, 80.70±2.75% (US+), free-microbubble; 62.89±3.12%, 92.10±6.04% (US+), PTX-NPs; 38.27±7.86%, 34.57±2.96% (US+), PTX-NPs-MBs; 41.42±12.24%, 26.69±0.69% (US+)

Experimental Example 7: Analysis of Infiltration Effects in Cancer Cells

Figure 8:
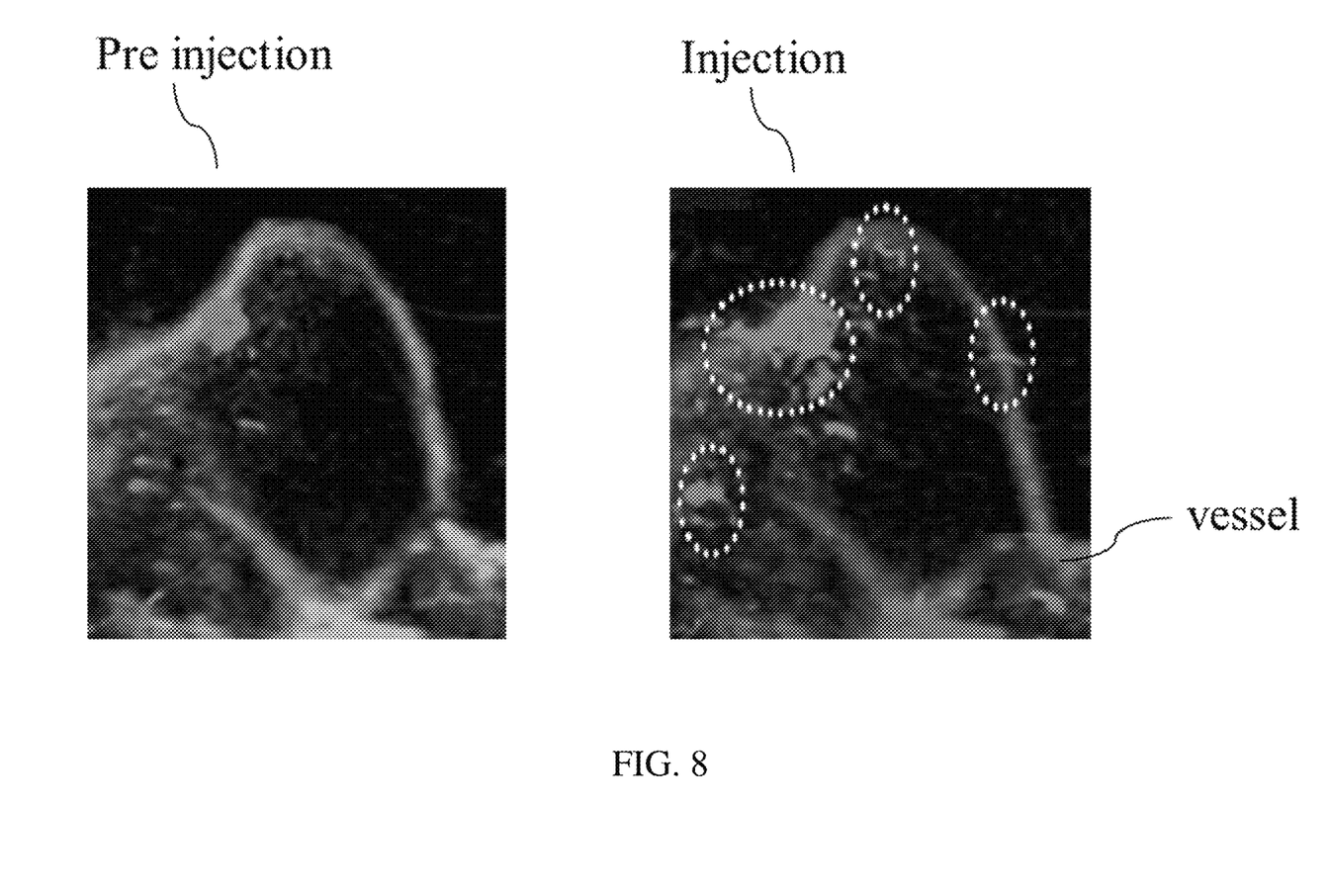
FIG. 8 illustrates data of producing photoacoustic images from cancer tissues in a disease animal model.

FIG. 8 illustrates data that cancer tissues were photoacoustic imaged in a disease animal model. It was confirmed that as the porphyrin MBs-NPs circulated in the blood vessels before and after the injection, the photoacoustic intensity was increased in the blood vessels.

What is claimed is:

1. A dual-purpose photoacoustic tomography (PAT)/ultrasound contrast agent for simultaneously conducting diagnosis and treatment of cancer, comprising:
   (a) a gas-filled microbubble comprising a porphyrin-lipid and a phospholipid compound including N-hydroxy succinimide (NHS); and
   (b) nanoparticles bound on a surface of the microbubble via an amide bond at a carboxyl group on the surface of the microbubble and a primary amine on the nanoparticle, wherein the nanoparticles comprise Human Serum Albumin (HSA) or a fragment thereof and containing an anticancer drug, have a diameter of 100 to 300 nm,
   and have a cross-linked structure formed by self-aggregation of the albumin or the fragment thereof.

2. The contrast agent of claim 1, wherein the drug is selected from the group consisting of docetaxel, cis-platin, camptothecin, paclitaxel, tamoxifen, anasterozole, gleevec, 5-fluorouracil (5-FU), floxuridine, leuprolide, flutamide, zoledronate, doxorubicin, vincristine, gemcitabine, streptozocin, carboplatin, topotecan, belotecan, irinotecan, vinorelbine, hydroxyurea, valrubicin, retinoic acid-series, methotrexate, meclorethamine, chlorambucil, busulfan, doxifluridine, vinblastine, mitomycin, prednisone, testosterone, mitoxantron, aspirin, salicylates, ibuprofen, naproxen, fenoprofen, indomethacin, phenyltazone, cyclophosphamide, mechlorethamine, dexamethasone, prednisolone, celecoxib, valdecoxib, nimesulide, cortisone, and corticosteroid.

3. The contrast agent of claim 1, wherein the microbubble is a gas-filled microsphere, a gas-filled liposome or a gas-forming emulsion.

4. The dual-purpose photoacoustic tomography (PAT)/ultrasound contrast agent of claim 1, wherein the microbubble has a diameter of 0.1 to 10 nm.

5. A method for preparing a dual-purpose photoacoustic tomography (PAT)/ultrasound contrast agent for simultaneously conducting diagnosis and treatment of cancer, the method comprising:
   (a) preparing each of a gas-filled microbubble and a nanoparticle containing an anticancer drug and having a diameter of 100 to 300 nm, wherein the microbubble contains a porphyrin-lipid and a phospholipid compound including N-hydroxy succinimide (NHS); and
   (b) mixing the nanoparticle and the microbubble at a predetermined ratio in water to effectively react a primary amine of the nanoparticle with the NHS to form an amide bond,
   wherein the nanoparticles include albumin and have a crosslinked structure formed by self-aggregation of the albumin, wherein the albumin is Human Serum Albumin (HSA) or a fragment thereof.

6. The method of claim 5, wherein the preparing of the microbubble further comprises:
   mixing an emulsifier with a third lipid, the porphyrin-lipid, the lipid comprising NHS, and an organic solvent to form a lipid thin film;
   putting the lipid thin film into water to hydrate the lipid thin film; and
   performing an ultrasound treatment thereon while injecting gas thereinto and maintaining high pressure.

7. The method of claim 6, wherein in the forming of the lipid thin film, the emulsifier:porphyrin-lipid:thirdlipid:lipid comprising NHS are added at a molar ratio of 5 to 10:15 to 30:60 to 75:15 to 30.

8. The method of claim 5, wherein the preparing of the nanoparticle comprises dissolving albumin in water, injecting a drug thereinto to prepare a mixture; adjusting a pH of the mixture to 7 to 9; and adding alcohol dropwise thereto, thereby forming self-aggregated albumin nanoparticles.

9. The method of claim 5, wherein the reacting comprises hydrolyzing the NHS to form a carboxyl group on a surface of the microbubble.

10. The method of claim 5, wherein the nanoparticle and the microbubble are reacted at a molar ratio of bonding reactive groups of 1:0.5 to 2.

* * * * *